United States Patent [19]

Nogier

[11] 4,161,943
[45] Jul. 24, 1979

[54] NEEDLE IMPLANTING APPARATUS

[76] Inventor: Paul Nogier, 108 rue du Dr. Edouard Locard, Lyon, France, 69005

[21] Appl. No.: 795,470

[22] Filed: May 10, 1977

[30] Foreign Application Priority Data

May 19, 1976 [FR] France .............................. 76 15861

[51] Int. Cl.$^2$ .......................................... A61B 17/52
[52] U.S. Cl. ................................ 128/1.3; 128/329 A
[58] Field of Search ................. 128/1.3, 2.1 C, 329 A, 128/217

[56] References Cited

U.S. PATENT DOCUMENTS

| 3,710,399 | 1/1973 | Hurst ..................................... 128/1.3 |
| 3,859,983 | 1/1975 | Dohring et al. ................... 128/2.1 C |
| 3,976,078 | 8/1976 | Toriello ............................ 128/329 A |
| 4,013,063 | 3/1977 | Bucalo .................................. 128/1.3 |

Primary Examiner—John D. Yasko
Attorney, Agent, or Firm—Dowell and Dowell

[57] ABSTRACT

An apparatus for implanting magnetized or magnetizable needles, which apparatus comprises a tubular body, means to support a flat needle of small dimensions, made of a magnetizable metal, and means to drive the said needle into the tissues. A permanent magnet, taking the form of a substantially circular flat tablet is inserted in closed end of the body with one of its sides exposed outwardly of same. When the needle has been implanted, it may be magnetized or remagnetized as often as required by merely applying the exposed side of the tablet against the tail of the needle. In a modification the body of the apparatus is provided with a socket-like protecting cap and the tablet is inserted in the closed end of this cap, the needle supporting means being so arranged that the tip of the needle is situated close to the said closed end of the cap in order to be already magnetized by the tablet before the needle is implanted.

6 Claims, 5 Drawing Figures

NEEDLE IMPLANTING APPARATUS

This invention relates to apparatus for the insertion of intra-dermal needles in order to achieve semi-permanent implants.

It is been demonstrated that the results obtained from such implants could be greatly improved by using magnetizable needles. Tests have also been made with previously magnetized needles. But metallic needles can only form rather poor permanent magnets owing to the proximity of their poles resulting from their small length. Ferrites are known which permit the manufacture of good permanent magnets with very close poles, but they do not lend themselves to the manufacture of small intra-dermal needles which should in practice be normally made of steel.

The West German Patent application No. 2,235,015 discloses the application of a magnetic field at acupuncture points by means of permanent magnets disposed close to these points. But these magnets should be retained in position, as for instance by adhesive tapes, and moreover this kind of treatment does not give as good results as implanted magnetized needles.

It is an object of the present invention to avoid this disadvantage.

In accordance with the invention, an apparatus for the insertion of intra-dermal needles also includes a permanent magnet by means of which the user may magnetize the implanted needle or maintain the magnetization thereof during the whole time of the treatment.

In a first embodiment of an apparatus according to the invention, the permanent magnet, taking the form of a circular tablet of reduced diameter, is disposed at the end of the apparatus opposed to the outlet through which the needle is introduced into the tissues. The needle is therefore initially unmagnetized or practically so. But once it has been implanted, the user may magnetize it and maintain its magnetization. For this purpose he reverses the apparatus and applies the circular tablet against the tail of the needle while rotating the apparatus about its axis.

In another embodiment the apparatus again includes a magnetized tablet, but the latter is disposed at the closed end of the protecting cap of the apparatus, this cap being of such length that the tablet is situated close to the tip of the needle retained in the body of the apparatus and thus acts on the latter to magnetize it and to maintain it magnetized until it is driven into the tissues. The user may thereafter use the cap to apply the tablet against the tail of the needle as with the first embodiment.

The tablet may be made of any appropriate material such as ferrites used either alone or in combination with plastics or rubber.

In accordance with another characteristic of the invention the circular tablet is so magnetized as to comprise on each of its sides two poles quite close to each other, each pole on one side of the table being disposed straight above or below a pole of opposed polarity on the other side.

Figure 3:
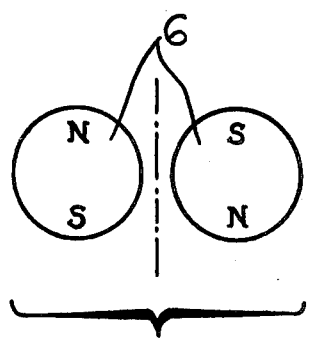

FIG. 3 indicates the arrangement of the poles on both sides of the magnetized tablet.

Figures 4, 5:
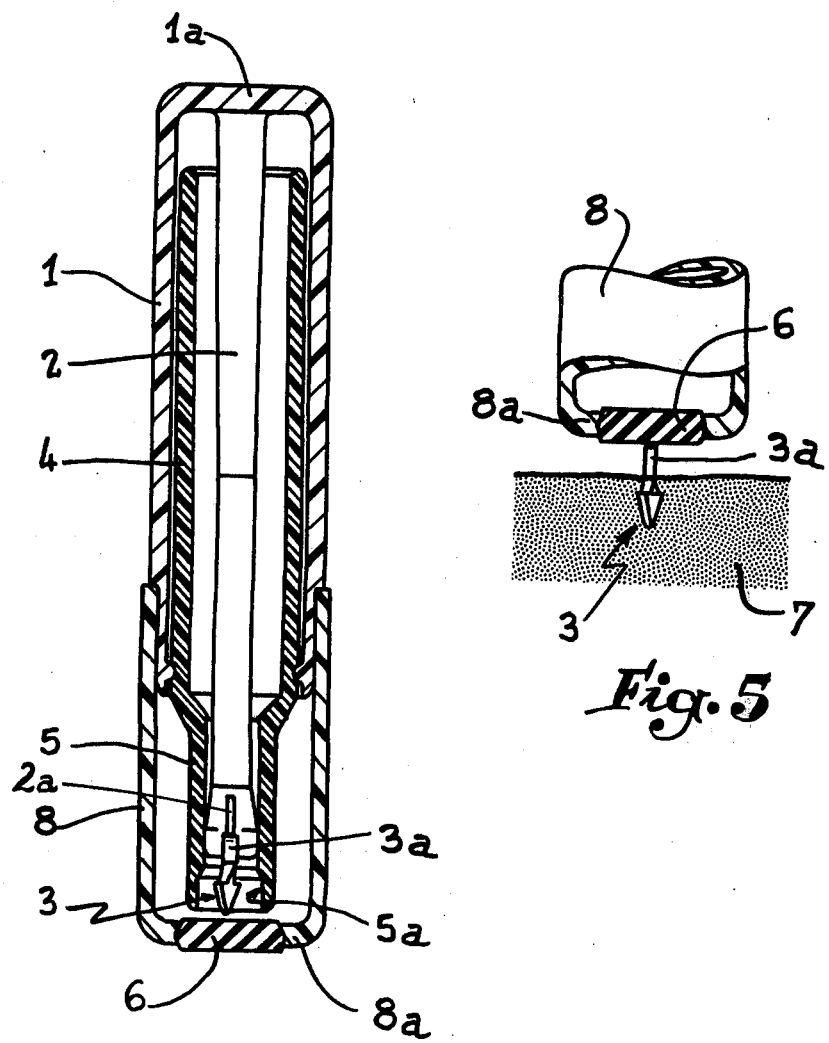

FIG. 4 is a longitudinal section of another embodiment.

FIG. 5 shows how this embodiment may be used.

Figure 1:
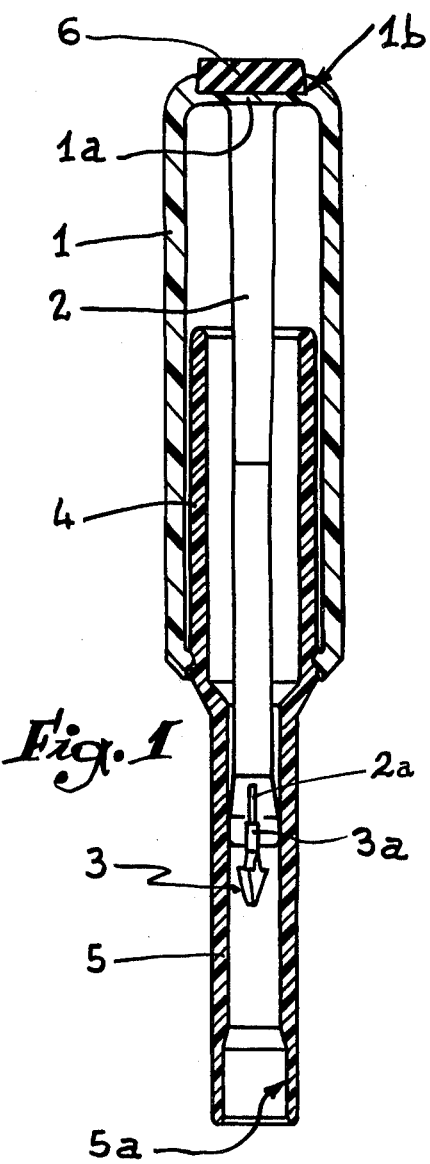
FIG. 1 is a longitudinal section of a first embodiment of an apparatus according to the invention.

The apparatus illustrated in FIG. 1 is of generally well-known type. It comprises an outer socket-shaped body 1 the closed end 1a of which is joined to an axial pusher 2 which extends beyond the open end of the said body, the end of the pusher supporting the tail of a flat needle 3 of quite small dimensions. Slidably disposed within this body 1 is a hollow cylindrical member 4 which extends outwardly in the form of a tubular portion 5. This portion surrounds the above-mentioned pusher 2 and it contracts the slotted end thereof on the tail 3a of the needle 3 to retain the latter within the apparatus. Portion 5 extends well beyond the needle and it comprises a free end 5a of enlarged inner diameter in which the slot 2a of the pusher may open to liberate the needle. In use this free end 5a is applied to the tissue at the point where the needle is to be introduced and the body 1 is pushed towards this point together with pusher 2 which drives the needle into the tissues. The apparatus may then be freely withdrawn since the slot 2a in which the needle tail 3a was clamped is no longer contracted by the zone of smaller inner diameter of portion 5.

In accordance with the invention the closed end 1a carries a small magnetized circular tablet 6. In the example illustrated the end 1a has for this purpose on its outer side a depression 1b in which the tablet is retained by any appropriate means, as for instance by being mounted as a force fit, or by an adhesive.

Figure 2:
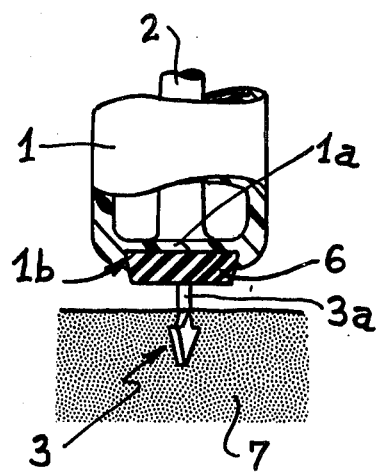
FIG. 2 illustrates how this apparatus should be used.

FIG. 2 shows how the apparatus of FIG. 1 should be used. Once the needle is implanted in the tissues 7 with its tail 3a protruding outwardly, the apparatus is reversed and the circular tablet 6 is applied against the aforesaid tail 3a to magnetize the needle. Experience demonstrates in this connection that the best results are obtained by rotating the tablet in contact with the needle tail.

Owing to the quite small dimensions of the needle, the magnetization thus realized disappears progressively, even if the needle is made of a steel of high remanence, but the magnetizing operation may be repeated as often as required during the treatment.

The circular tablet 6 may be made of any suitable material and more particularly of ferrites to permit a relatively strong and permanent magnetization in spite of the small distance between its poles. In actual practice very good results have been obtained with a rubber containing such ferrites in pulverulent form. The poles may be disposed respectively in the center of one or the other side of the tablet. It is however preferable to provide two poles on each side, the North pole on one side being straight below or above the South pole on the other side, as indicated by the letters N and S in FIG. 3.

In the embodiment of FIG. 4 the apparatus comprises a protecting cap 8 having a closed end 8a in which the magnetized tablet 6 is inserted in such a manner that both its inner and outer sides are exposed. The length of cap 8 is such that the said tablet is close to the free end 5a of tubular portion 5 when the body is closed by the cap. Moreover this end 5a is relatively short and the slotted end of pusher 2 is situated close to this free end 5a as shown in FIG. 4 in such a manner that the tip of needle 3 is at a very short distance from the inner side of the circular tablet 6.

With such an arrangement the needle 3 is magnetized by tablet 6 and this magnetization is maintained as long as the needle remains enclosed in the apparatus. When it has been implanted in the tissues, it may be re-magnetized as often as required by again applying tablet 6 against the tail of the needle (FIG. 5) and by rotating cap 8.

It will be understood that in the embodiment of FIG. 4 the inner side of tablet 6 could be covered by a thin layer of plastics. In other words the closed end 8a of cap 8 could be formed with a depression to receive tablet 6 as in the case of FIG. 1, provided the thickness of the bottom of this depression is relatively slight.

I claim:

1. In an apparatus to introduce intra-dermal needles in the tissues, said apparatus including a body, supporting means carried by said body to support a needle made of a magnetizable material, and means to push said needle beyond said body to implant same into the tissues, the improvement in said apparatus comprising a permanent magnet fixed to said apparatus on an exposed surface thereof by means of which the implanted needle may be magnetized and remagnetized as often as required.

2. In an apparatus as claimed in claim 1, said body including a portion of tubular shape with a closed end, said permanent magnet being in the form of a substantially circular flat tablet with first and second sides and with at least one pole on said first side, and said tablet being secured to said closed end with said first side being exposed outwardly of said body.

3. In an apparatus as claimed in claim 2, said closed end having inner and outer sides, said outer side comprising said exposed surface and being formed with a depression, and said tablet being disposed in said depression.

4. In an apparatus as claimed in claim 1:
said body being of tubular shape with an open end;
said apparatus further including a socket-shaped cap to close said open end of said body when said apparatus has not yet been used, with said cap having a closed end;
said permanent magnet being in the form of a substantially circular flat tablet with first and second sides and with at least one pole on each of said sides, and said tablet being secured to said closed end of said cap with said first side being exposed outwardly of said cap;
said needle having a tip and a tail portion retained by said supporting means;
and said supporting means being so arranged in said body that when said apparatus has not yet been used the tip of said needle is close to the closed end of said cap to be magnetized by said tablet.

5. In an apparatus as claimed in claim 4, said closed end of said cap having a central opening and said tablet being disposed within said opening with its first and second sides respectively exposed outwardly and inwardly of the said cap.

6. In an apparatus as claimed in claim 1, said permanent magnet being in the form of a substantially circular flat tablet having first and second sides substantially parallel to each other with a North and a South pole on each of said sides, the North pole of each one of said sides being disposed substantially on the same line perpendicular to said sides as the South pole of the other one of said sides.

* * * * *